United States Patent [19]

Cywinski

[11] 4,181,809

[45] Jan. 1, 1980

[54] PRODUCTION OF TERTIARY-BUTYL METHYL ETHER

[75] Inventor: Norbert F. Cywinski, Odessa, Tex.

[73] Assignee: El Paso Products Company, Tex.

[21] Appl. No.: 956,027

[22] Filed: Oct. 31, 1978

[51] Int. Cl.² .................. C07C 41/00; C07C 41/06
[52] U.S. Cl. ................................................ 568/671
[58] Field of Search ........................ 568/671, 697; 260/449 R

[56] References Cited

U.S. PATENT DOCUMENTS

| | | | |
|---|---|---|---|
| 1,836,085 | 12/1931 | Patart | 260/449 R |
| 1,984,884 | 12/1934 | Lazier | 260/449 R |

*Primary Examiner*—Howard T. Mars

[57] ABSTRACT

This invention provides a process for producing tertiary-butyl methyl ether which involves contacting a mixture of isobutylene and synthesis gas with a catalyst under modified methanol synthesis processing conditions.

6 Claims, 1 Drawing Figure

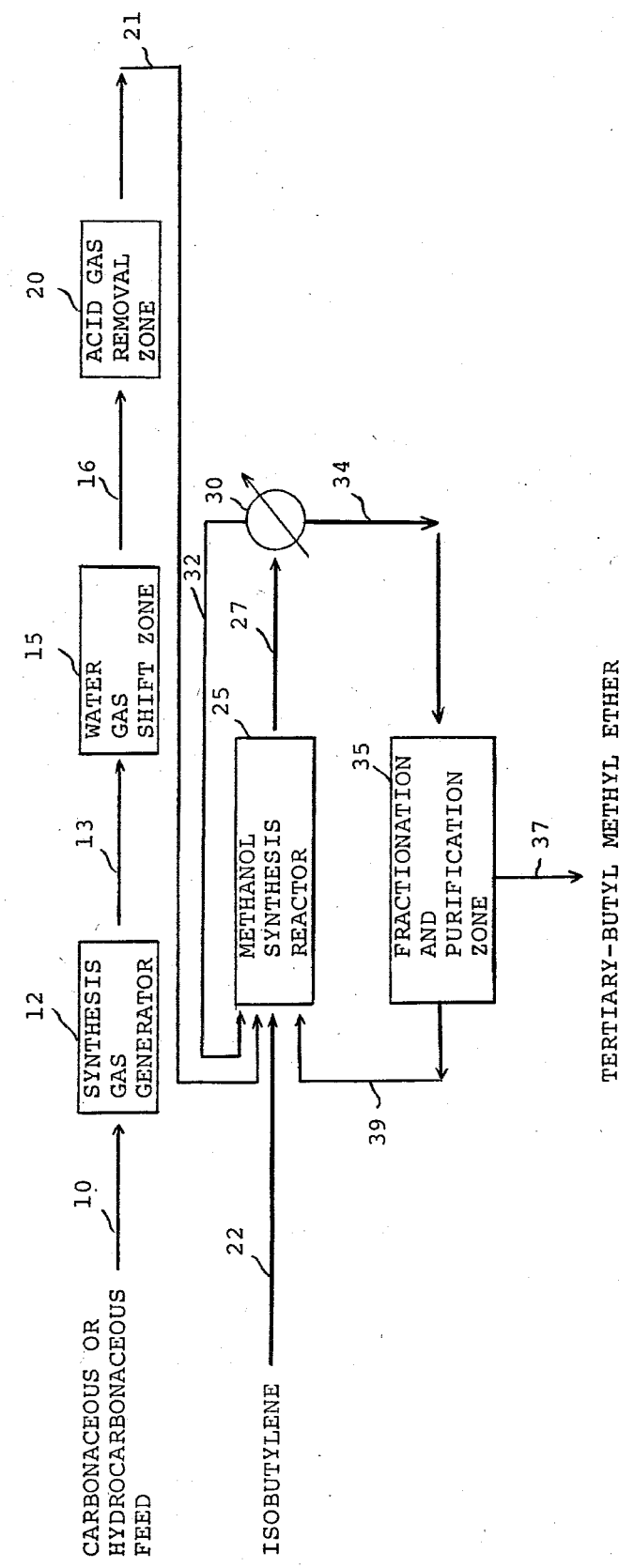

PRODUCTION OF TERTIARY-BUTYL METHYL ETHER

BACKGROUND OF THE INVENTION

There are several methods reported in the chemical literature for the synthesis of tertiary-butyl methyl ether. In one method, the product is produced by the dehydration-condensation of tertiary-butanol with methanol.

U.S. Pat. No. 2,065,540 discloses the reaction of isobutylene with methanol in the presence of boron trifluoride under mild conditions of temperature and pressure to yield tertiary-butyl methyl ether.

U.S. Pat. No. 2,544,392 discloses a method for producing tertiary-butyl methyl ether which involves passing a vapor mixture of isobutylene and methanol over a basic catalyst (e.g., activated magnesia impregnated with an alkali metal hydroxide) at a temperature of about 200° C. and a pressure of about 200 psig, wherein the volume space velocity is adjusted to provide a contact time of at least several minutes.

U.S. Pat. No. 2,721,222 is directed to a method for the preparation of tertiary-butyl methyl ether by the reaction of isobutylene with methanol in the presence of sulfuric acid, and recovery of the product from the reaction mixture by dilution of the mixture with methanol followed by distillation. U.S. Pat. No. 3,135,807 describes a process for the manufacture of tertiary-butyl methyl ether by the reaction of an equimolar mixture of isobutylene and methanol at a temperature of about 100°–400° F., a pressure of about 25–1000 psig and a volume space velocity of about 0.1–5 hr.$^{-1}$ in the presence of a catalyst selected from bismuth molybdate and the lead, antimony, tin, iron, cerium, bismuth, nickel, cobalt and thorium salts of phosphomolybdic acid.

U.S. Pat. No. 3,718,701 discloses a method for producing an ether such as tertiary-butyl methyl ether, by reacting an olefin and an alkanol in the liquid phase at a temperature of about 0°–350° C. and a pressure of about 1–10,000 atmospheres in the presence of a catalytic amount of a homogeneous catalyst such as platinum chloride.

Other prior art procedures relating to the production of ethers by the interaction between an olefinic hydrocarbon and an alkanol are disclosed in U.S. Pat. Nos. 3,170,000; 3,267,156; 3,821,315; 3,825,603; and the like.

There remains a need for an efficient and economical process for the production of tertiary-butyl methyl ether from readily available starting materials.

Accordingly, it is an object of this invention to provide a process for producing tertiary-butyl methyl ether which is adapted for continuous vapor phase operation.

It is another object of this invention to provide a process for producing tertiary-butyl methyl ether by the interaction of isobutylene with synthesis gas.

Other objects and advantages of the present invention will become apparent from the accompanying description and examples.

DESCRIPTION OF THE INVENTION

One or more objects of the present invention are accomplished by the provision of a process for producing tertiary-butyl methyl ether which comprises contacting a mixture of isobutylene and synthesis gas with a methanol synthesis catalyst at a temperature between about 200° C. and 400° C. and a pressure between about 100 and 5000 psi.

As described more fully hereinafter, the processing conditions and the catalyst are selected to shift the competing reaction equilibria in favor of tertiary-butyl methyl ether production. An essential aspect of the invention process is the in situ production of methanol. Under the processing conditions, as the methanol is formed it interacts with the isobutylene component of the feed stream to yield the desired tertiary-butyl methyl ether:

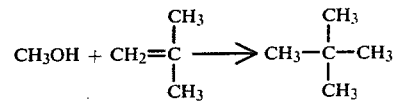

The in situ production of methanol involves three synthesis gas hydrogenation mechanisms:

1. $CO + 2H_2 \rightarrow CH_3OH$

2. $CO_2 + 3H_2 \rightarrow CH_3OH + H_2O$

3. $CO_2H_2 \rightleftharpoons CO + H_2O$

The synthesis gas employed in the invention process, consisting principally of hydrogen and carbon monoxide, is conventionally derived by the partial oxidation of a hydrocarbonaceous fuel in a free-flow noncatalytic refractory lined synthesis gas generator (U.S. Pat. No. 2,992,906). The produced synthesis gas generally is too rich in hydrogen for the stoichiometry of the methanol synthesis reaction. This can be remedied by adding extraneous carbon dioxide to the synthesis gas to achieve a suitable hydrogen/carbon oxides balance.

The presence of carbon dioxide in the feed stream has additional advantages in the practice of the present invention process, because it tends to suppress undesirable side reactions such as hydrogenation of the isobutylene component to isobutane, or hydroformylation of the isobutylene component to the corresponding aldehydes and alcohols.

Any conventional reactor may be employed for the present invention process, such as single and multiple methanol synthesis catalytic reactors which are described in U.S. Pat. Nos. 3,666,423; and 3,993,457; and French Pat. No. 1,497,109.

U.S. Pat. No. 3,666,423 describes a methanol synthesis reactor in which two sets of heat exchanges are embedded in a catalyst and there is heat exchange between fresh and reacted gases. The feed stream is passed through the inside of the heat exchangers and is preheated by indirect heat exchange with gases reacting on the outside of the heat exchangers. The preheated feed stream is then passed through the methanol synthesis catalyst on the outside of the heat exchangers where said exothermic reaction occurs.

By the term "methanol synthesis catalyst" is meant the catalyst systems known and used in the art for the conversion of synthesis gas to methanol. Illustrative of preferred methanol synthesis catalysts are those described in U.S. Pat. No. 3,920,717.

A typical methanol synthesis catalyst is selected from zinc oxide, copper oxide and mixtures thereof plus a promoter selected from the group of oxides consisting of magnesium, aluminum, chromium, and mixtures thereof. For high pressure operation (i.e. above 200 atmospheres) zinc and chromium oxides may be produced by treating aqueous zinc and chromium nitrate solutions with ammonium hydroxide to produce the hydroxide precipitates and then calcining the precipitates. Preferably, the Cr/Zn atomic ratio of the catalyst is in the range of about 0.5–1.5. While lower ratios result in lower conversion to methanol they provide better selectivity. For example, a zinc oxide catalyst containing 11 weight percent chromium oxide may yield methanol up to 99 percent purity at about 375° C. and 200 atmospheres in a conventional methanol synthesis operation. Suitable promoters for zinc and chromium oxides include magnesium, iron and manganese.

Copper-containing catalysts generally have a higher activity and greater rate of reaction than that of zinc-chromium oxides. However, they have lower heat resistance and are highly sensitive to poisoning by sulfur, carbonyl-containing compounds, phosphorus and chlorine. A typical composition consists of 90 parts by weight of copper oxide and 10 parts chromium oxide. They are generally used for operation at low pressure, e.g. less than about 110 atmospheres and temperatures below 370° C. 20–30% conversions of synthesis gas to methanol may be obtained with alkali promoted copper catalysts at about 230° C., 100 atmospheres, and a space velocity of 10,000 standard cubic feet per hour (SCFH) per cubic foot of catalyst. Sulfur content of the synthesis gas should be less than 5 parts per million (ppm), preferably less than 2 ppm, and advantageously less than 0.1 ppm of sulfur.

Preferred compositions of ternary catalysts of copper, zinc, and chromium oxides as a percentage of metal atoms are in the range of Cu, 90 to 20; Zn, 8 to 60; and Cr, 2 to 30. The catalyst may be prepared by coprecipitation from a nitrate solution by addition of a carbonate solution. The precipitate is washed, dried, and calcined at a temperature below 400° C. With a synthesis gas composition in mole percent comprising $H_2$, 75; CO, 15; and $CO_2$, 10 reacting in contact with this catalyst at a temperature of about 250° C., and a pressure of about 50 atmospheres, and a space velocity in the range of about 16,000 to 25,000 hr.$^{-1}$, about 15 percent of the Co in the feed may be converted to raw methanol containing less than about 0.5 percent organic impurities.

Other suitable methanol synthesis catalysts for the practice of the present invention process include copper/aluminum/zinc mixtures, and the catalyst compositions disclosed in U.S. Pat. Nos. 1,741,306; 3,326,956; 3,709,919; 3,888,896; 3,894,102; 3,897,471; 3,923,694; 4,011,275; and references cited therein; incorporated herein by reference.

In conventional synthesis gas conversion processes for producing methanol, the stoichiometry of the synthesis gas is adjusted so that there are about two moles of hydrogen per mole of carbon monoxide. The synthesis gas is passed into effective contact with a methanol synthesis catalyst whereby a portion of the synthesis gas is converted to methanol. Normally the reaction is operated at considerably elevated temperatures and pressures and with relatively low conversion per pass. For the purposes of the present invention process, there are several departures from typical methanol synthesis processing parameters required in order to control the reaction thermodynamics in favor of the selective production of tertiary-butyl methyl ether.

Hence, the feed mixture employed in the present invention process preferably contains hydrogen and carbon monoxide in a molar ratio between about 0.8 and 3 to 1 of hydrogen to carbon monoxide, and most preferably a molar ratio between about 0.8 and 2.

As mentioned previously, the additional presence of carbon dioxide in the feed mixture is advantageous in the invention process. When carbon dioxide is present, the preferred molar ratio in the feed mixture is between about 1 and 5 to 1 of hydrogen to the combined molar proportions of carbon oxides. The quantity of carbon dioxide in the feed mixture can vary in the range between about 0.5 to 2 moles per mole of carbon monoxide contained therein. The greater molar specific heat of carbon dioxide relative to carbon monoxide and the lower heat of reaction of carbon dioxide in the methanol synthesis provide a more uniform temperature control in the reaction system, and the life of the methanol synthesis catalyst is increased. It also appears that carbon dioxide suppresses the formation of dimethyl ether.

The content of isobutylene in the feed mixture is preferably maintained at the minimal level sufficient to satisfy the stoichiometry of the overall process. Since the typical conversion of carbon oxides is in the range between about 5 and 30 mole percent per pass, the isobutylene advantageously can be maintained in the range between about 0.1 and 1 mole per mole of carbon oxides in the feed mixture. The feed mixture can also contain minor quantities of nitrogen, argon, methane, water, and the like, without deleterious effect.

The isobutylene/synthesis gas feed stream can be passed through the catalytic reaction zone at a volume space velocity between about 2000 hr.$^{-1}$ and 20,000 hr.$^{-1}$. The reaction zone temperature is maintained in the range between about 200° C. and 400° C., and the pressure is maintained in the range between about 100 and 5000 psi. The space velocities are on the basis of standard conditions of one atmosphere and 0° C.

The effluent from the reaction zone can be heat exchanged with a portion of the incoming feed stream to preheat said feed stream prior to its introduction into the catalytic reaction zone. The partially cooled effluent stream can then be water-cooled to condense the tertiary-butyl methyl ether, methanol, water and other normally liquid components of the effluent stream. The uncondensed gaseous components nominally will consist of hydrogen, carbon monoxide, carbon dioxide and isobutylene, and minor amounts of methane, hydrogen sulfide, isobutane and dimethyl ether. This gaseous mixture can be recycled without further treatment, or it can be subjected to conventional procedures for reduction of the carbon dioxide and hydrogen sulfide content or removal of the dimethyl ether, carbonyl, formal, isobutanol, and other oxygenated organic impurities. Any methanol recovered during the product effluent fractionation procedures can be recycled in the process.

Since the processing parameters which favor methanol synthesis are not the most favorable for the interaction of isobutylene with methanol to produce tertiary-butyl methyl ether, superior results can be obtained by further modification of the reaction conditions previously described hereinabove. Thus, in another embodiment this invention provides a continuous process for producing tertiary-butyl methyl ether which comprises contacting a stream of isobutylene and synthesis gas with a methanol synthesis catalyst in a two zone methanol synthesis reactor, wherein the first zone of the reactor is maintained at a temperature between about 200° C. and 350° C. and a pressure between about 500 and 2000 psi, and the volume space velocity in the first zone is between about 2000 hr.$^{-1}$ and 20,000 hr.$^{-1}$, and the second zone of the reactor is maintained at a temperature between about 150° C. and 300° C. and a pressure between about 100 and 1000 psi, and the volume space velocity in the second zone is between about 10 hu.$^{-1}$ and 1000 hr.$^{-1}$; fractionating the reactor effluent to separate tertiary-butyl methyl ether as a product; and recycling unreacted isobutylene, carbon oxides and methanol to the methanol synthesis reactor.

In a further embodiment of this invention, in the said second zone recited above the methanol synthesis catalyst can be admixed with or replaced by an ether synthesis catalyst. By the term "ether synthesis catalyst" is meant the types of catalysts which are known and used in the prior art for catalyzing vapor phase reaction of olefins with alkanols. Illustrative of ether synthesis catalysts are activated alkaline earth metal oxides, and the catalysts disclosed in U.S. Pat. Nos. 3,135,807; 3,821,315; and 3,825,603; incorporated herein by reference.

The following description is directed to the FIGURE, which is a schematic flowsheet of an embodiment of the present invention process. The description has been simplified by omitting any reference to processing equipment such as valves, pumps, compressors, heat exchangers, and the like.

The carbonaceous or hydrocarbonaceous feed referred to in the FIGURE can be any of gaseous, liquid and solid hydrocarbon and carbonaceous materials. Illustrative of such feed materials are pumpable slurries of coal, petroleum coke, concentrated sewage sludge, and the like; and petroleum distillates and residues, asphalt, tar sand, shale oil, coal tar, methane, natural gas, coke oven gas, refinery gas, and the like. The feed material can include paraffinic, olefinic (e.g., isobutylene), naphthenic and aromatic constituents in any proportions.

The feed material is introduced through line 10 into Synthesis Gas Generator 12, where the feed material is contacted with steam (500°–1200° C. and 50–1500 psig) to form a crude synthesis gas consisting of hydrogen, carbon monoxide, carbon dioxide, methane, hydrogen sulfide and water. The crude synthesis gas is transferred via line 13 to Water Gas Shift Zone 15. A portion of the carbon monoxide is reacted with steam (250°–450° C., 50–1500 psig) in Zone 15 to form hydrogen and carbon dioxide. The shifted gas is passed through line 16 into Acid Gas Removal Zone 20, where gas purification is accomplished by refrigeration and physical or chemical absorption with a solvent, such as methanol or triethanolamine, or alternatively with hot potassium carbonate. Hydrogen sulfide is substantially removed in Zone 20, and the carbon dioxide content is reduced to a desired level. The purified synthesis gas exits from Zone 20 via line 21 and is introduced into Methanol Synthesis Reactor 25, where the synthesis gas is converted into methanol (200°–350° C., 500–2000 psig), and the methanol reacts with isobutylene, which has been entered into Reactor 25 via line 22, to form tertiary-butyl methyl ether. The product effluent exits from Reactor 25 via line 27 and passes through a cooler and knock-out device 30, where the normally liquid products of the effluent stream are condensed. Unconverted gases are passed overheat through line 32 and recycled to Reactor 25. The normally liquid product mixture recovered in device 30 is passed through line 34 into Fractionation and Purification Zone 35. Purified tertiary-butyl methyl ether from Zone 35 is passed through line 37 to storage, and methanol recovered in Zone 35 is recycled to Reactor 25 via line 39.

The following examples are further illustrative of the present invention. The reactants and other specific ingredients are presented as being typical, and various modifications can be devised in view of the foregoing disclosure within the scope of the invention.

EXAMPLE I

This Example illustrates the preparation of a methanol synthesis catalyst.

A 1450 gram quantity of $Cu(NO_3)_2.3H_2O$ and a 892.5 gram quantity of $Zn(NO_3)_2.6H_2O$ are dissolved in 18 liters of water.

A second solution is prepared by dissolving 140 grams of $NaVO_3.H_2O$ and 900 grams of $Na_2CO_3$ in 18 liters of water.

Both solutions are heated to 80° C., and the nitrate solution is added with stirring to the vanadate solution. The resulting precipitate is recovered by filtration, washed and dried.

The dried catalyst precursor is calcined at 300° C. for several hours, then ground and admixed with 2% graphite before compressing into pellets.

The catalyst thus produced contains 60 atomic percent copper, 30 atomic percent Zn and 10 atomic percent vanadium.

EXAMPLE II

This Example illustrates the preparation of a methanol synthesis catalyst in accordance with U.S. Pat. No. 3,923,694.

A solution of 387 grams of sodium aluminate in 2000 milliliters of water is admixed with 1100 milliliters of 70% nitric acid. To the resulting solution is added a solution of 597 grams of zinc nitrate hexahydrate in 500 milliliters of water.

The solution is heated at 85° C. and admixed with a molar solution of sodium carbonate at a rate to yield a slurry having a pH of 6.5. The resulting precipitate is filtered and washed.

A 1394 gram quantity of the precipitate is slurried in 3000 milliliters of water, and then mixed with a 1200 milliliters solution containing 435 grams of cupric nitrate trihydrate and 134 grams of zinc nitrate. The slurry is heated to 85° C. and admixed with a molar solution of sodium carbonate to yield a slurry having a pH of 6.5. The slurry is warmed at 85° C. with gentle stirring, and then the slurry is filtered and the precipitate washed to decrease the $Na_2O$ content.

The dried catalyst precursor is calcined at 300° C. for several hours, then crushed, mixed with 2 percent graphite and pelleted.

The catalyst has the following weight percent composition:
CuO: 60.1
ZnO: 22.2
$Al_2O_3$: 7.9
$Na_2O$; 0.03

This corresponds to an atomic ratio of approximately $Cu_6Zn_{2.33}Al_{1.67}$. At least a portion of the Zn/Al is in the form of spinel crystallites.

EXAMPLE III

This Example illustrates the production of tertiary-butyl methyl ether in accordance with the present invention process.

A methanol synthesis catalyst of the type illustrated in Example II is charged to a tube reactor adapted for continuous operation.

A gas mixture of isobutylene and synthesis gas is passed through the reactor at a temperature of 300° C. and a pressure of 750 psig. The space velocity is 9000 volumes of reactants per volumes of catalyst per hour, measured at standard conditions. The composition of the feed mixture is as follows on a volume basis:

$H_2$: 40%
CO: 20%
$CO_2$: 10%
$C_4H_8$: 30%

About 5–30 percent of the isobutylene is reacted per pass, with a conversion efficiency to tertiary-butyl methyl ether of about 40–70 percent.

The efficiency of the isobutylene conversion to tertiary-butyl methyl ether is increased if the catalyst bed is divided into two zones, and in the first zone the temperature is about 300° C., the pressure is about 750 psig, and the space velocity is about 15,000 $hr.^{-1}$; and in the second zone the temperature is about 200° C., the pressure is about 500 psig, and the space velocity is about 100 $hr.^{-1}$.

What is claimed:

1. A process for producing tertiary-butyl methyl ether which comprises contacting a mixture of isobutylene and synthesis gas with a methanol synthesis catalyst at a temperature between about 200° C. and 400° C. and a pressure between about 100 and 5000 psi.

2. A process in accordance with claim 1 wherein the synthesis gas additionally contains carbon dioxide.

3. A process in accordance with claim 1 wherein the methanol synthesis catalyst is selected from oxides of zinc and copper, and mixtures thereof.

4. A process in accordance with claim 3 wherein the methanol synthesis catalyst contains a promotor selected from oxides of chromium, magnesium, aluminum, and mixtures thereof.

5. A continuous process for producing tertiary-butyl methyl ether which comprises contacting a stream of isobutylene and synthesis gas with a methanol synthesis catalyst in a two zone methanol synthesis reactor, wherein the first zone of the reactor is maintained at a temperature between about 200° C. and 350° C. and a pressure between about 500 and 2000 psi, and the volume space velocity in the first zone is between about 2000 $hr.^{-1}$ and 20,000 $hr.^{-1}$, and the second zone of the reactor is maintained at a temperature between about 150° C. and 300° C. and a pressure between about 100 and 1000 psi, and the volume space velocity in the second zone is between about 10 $hr.^{-1}$ and 1000 $hr.^{-1}$; fractionating the reactor effluent to separate tertiary-butyl methyl ether as a product; and recycling unreacted isobutylene, carbon oxides and methanol to the methanol synthesis reactor.

6. A process in accordance with claim 5 wherein the methanol synthesis catalyst in the said second zone is admixed with or replaced by an ether synthesis catalyst.

* * * * *

UNITED STATES PATENT OFFICE
CERTIFICATE OF CORRECTION

Patent No. 4,181,809          Dated January 1, 1980

Inventor(s) Norbert F. Cywinski

It is certified that error appears in the above-identified patent and that said Letters Patent are hereby corrected as shown below:

Column 2, line 12, in the formula,

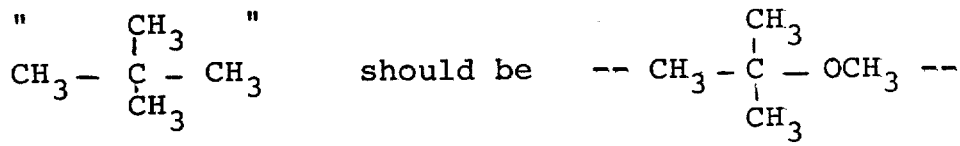

Column 4, line 68, "2000 hr.⁻" should be -- 2000 hr.$^{-1}$ --.

Column 5, line 4 "10 hu.$^{-1}$" should be -- 10 hr.$^{-1}$ --.

Column 5, line 64 "overheat" should be -- overhead --.

Column 7, line 24, "100 hr.$^{31\ 1}$" should be -- 100 hr.$^{-1}$ --.

Column 8, line 18, "20,000 hr.$^{31\ 1}$" should be -- 100 hr.$^{-1}$ --.

Signed and Sealed this

First Day of April 1980

[SEAL]

Attest:

SIDNEY A. DIAMOND

Attesting Officer          Commissioner of Patents and Trademarks